United States Patent
Beyer

(10) Patent No.: US 7,908,943 B2
(45) Date of Patent: Mar. 22, 2011

(54) OBLIQUE TATTOO MACHINE

(76) Inventor: Roald Beyer, Munich (DE)

( * ) Notice: Subject to any disclaimer, the term of this patent is extended or adjusted under 35 U.S.C. 154(b) by 49 days.

(21) Appl. No.: 11/656,026

(22) Filed: Jan. 22, 2007

(65) Prior Publication Data

US 2008/0200942 A1  Aug. 21, 2008

(51) Int. Cl.
*B43K 5/00* (2006.01)
*B26F 1/00* (2006.01)
*A61B 17/34* (2006.01)

(52) U.S. Cl. .............. 81/9.22; 30/362; 606/186

(58) Field of Classification Search .............. 81/9.22; 30/362; 606/186
See application file for complete search history.

(56) References Cited

U.S. PATENT DOCUMENTS

| | | | |
|---|---|---|---|
| 196,747 | A | 4/1877 | Edison |
| 464,801 | A | 7/1891 | O'Reilly |
| 4,159,659 | A * | 7/1979 | Nightingale .............. 81/9.22 |
| 5,054,339 | A | 10/1991 | Yacowitz |
| 5,551,319 | A | 9/1996 | Spaulding |
| 6,282,987 | B1 | 4/2001 | Moniz |

OTHER PUBLICATIONS

Machinegun Magazine, 2001, pp. 5-7,issue 1. Eikon Device inc., Kingston ON Kanada.
Machinegun Magazine, Feb. 2002, pp. 14-15, 28-29.issue 2. Eikon Device inc , Kingston ON Kanada.
Machinegun Magazine,Nov. 2003. pp. 10-13: 20-21;30-33; 34-35 ,issue 4, Eikon Device inc . Kingston ON Kanada.
Machinegun Magazine,Aug. 2004, pp. 6-8; 10-21;28-33;36;38-39;45-47,issue 5, Elkon Device inc., Kingston ON Kanada.
Machinegun Magazine,Sep. 2005, pp. 7-9;29-31 ,issue 6, Eikon Device inc., Kingston ON Kanada.
Machinegun Magazine, Sep. 2006, pp. 16-22; 24-27; 40-46,issue 7 , Eikon Device inc , Kingston ON Kanada.

* cited by examiner

*Primary Examiner* — Hadi Shakeri
(74) *Attorney, Agent, or Firm* — Anthony H. Handal; Handal & Morofsky, LLC

(57) ABSTRACT

Through putting the coils of a tattoo machine in an angle and mounting an equivalently bent hammer on a, although in a (little more than the before mentioned ones), angle fixed spring mount we obtain a machine that is stronger than other machines compared in size and lighter and shorter than other machines that are comparable in power.

A marking device with an oscillating needle. The needle is attached through a needle bar on an armature bar which is attracted by an electromagnetic assembly. A from rear to front ascending angled stair-like milled yoke supports the electromagnetic assembly, which consists of one lower and one higher coil. A spring mount with an adequate angle is mounted to the side plates. An inversely proportional bent armature bar levels that before mentioned angle. The armature bar is attached through a spring to the spring mount. The angle of the set-up procures the oscillating armature bar with a both forth and downward motion, following a so called arc principle. The air gap between the front coil and the armature bar is effectively smaller. The needle hits the skin not in a straight motion but in a diving motion. Thus, the resistance of the skin is easier to overcome.

6 Claims, 2 Drawing Sheets

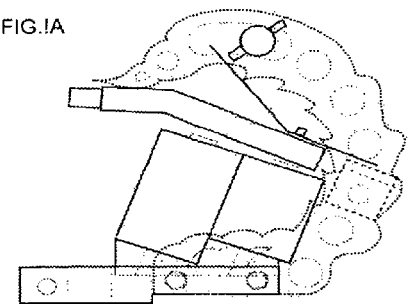
FORWARD ←·············································→ BACKWARD
FIG.1A
FIG.1B
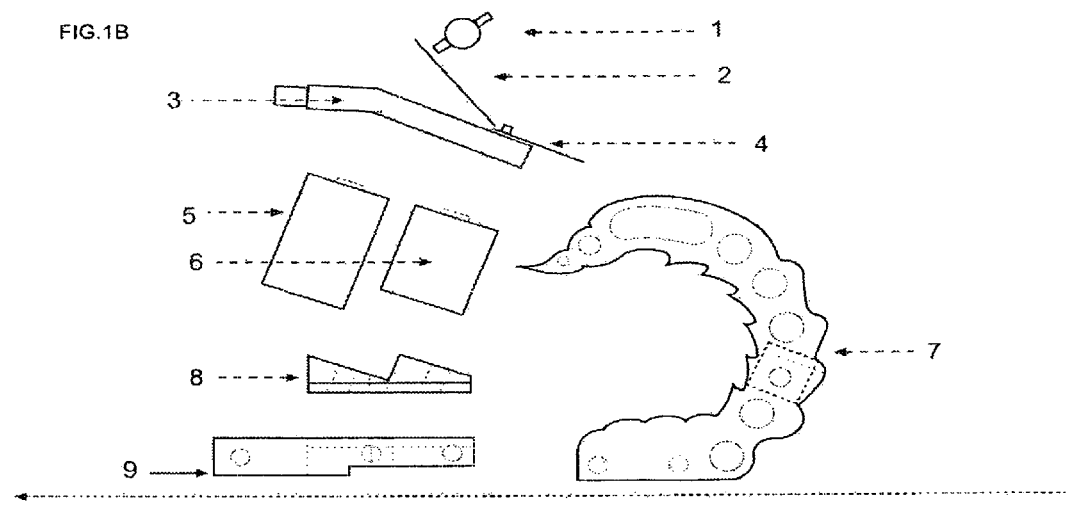
CONVENTIONAL TATTOO MACHINE
FIG.1C
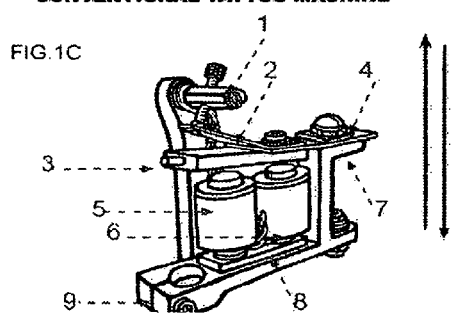
INVENTED TATTOO MACHINE
FIG.1D
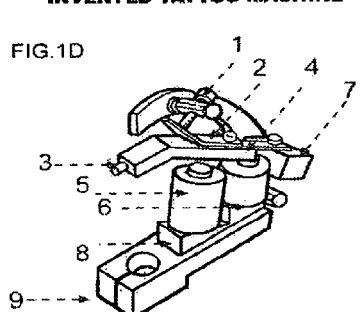

FORWARD ← - - - - - - - - - - - - - - - - - - - → BACKWARD

OBLIQUE TATTOO MACHINE

CROSS-REFERENCE TO RELATED APPLICATIONS

Not Applicable

STATEMENT TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING CD APPENDIX

Not Applicable

THE NAMES AND PARTIES TO A JOINT RESEARCH AGREEMENT

Not Applicable

INCORPORATION-BY-REFERENCE OF MATERIAL SUBMITTED ON A COMPACT DISC

Not applicable

US Patent class is No 81, subclass 9.22.

In the field of tattooing, like everywhere else, there is the time factor. To get bigger and wider spaces inked or colored in a shorter period of time there have been some approaches in the last years to solve that problem. Needlegroups, going up to an inch in width have been invented.

Since there's some tolerance of the skin concerning the maximum pressure, the edges of those needlegroups are rounded, in this way the pressure of the needles is not lying on the outer edges of the needle groups and thus not cutting the skin.

At the same time people were working on faster machines and a correct set-up since supplying the machine with more voltage does not make the machine run faster but only harder.

But in this field again there's limitations of the skin, what it can bear, both in faster and harder impact of the needles.

There's a quite fine line between not bringing in the color and destroying the tissue.

Most conventional coil powered machines (driven by electromagnetic induction) do not have the strength to pull those big needles, from now on called magnums, since by the augmenting width of the needle group
a) the friction between needle and needle holding tube, from now on called tube, gets higher and
b) the resistance of the skin against the penetration gets higher, too.

To solve this problem some people made up their mind to build machines, that got a bigger leverage effect permitting to use the existent power to overcome that skin resistance more easily, permitting those machines to work with big magnums.

Between others the stroke defines the set-up of a machine. The stroke depends on how big the air gap is (which is defined as the way from the point where the Hammer is when it is not attracted by magnetism- and the front coil) and on the length of the lever bar, the longer the lever bar the smaller the air gap has to be to achieve equivalent stroke as a shorter Hammer.

Those machines have a longer lever bar, the so called hammer, but at the same time those machines are loner themselves, too, which makes it a little bit hard to work for longer periods of time since the coils sit at the rear end of the machine while the tube, which is the handle of the machine, sits on the front end, creating a negative leverage on the hand.

Which basically means those machines might be faster with coloring the skin, but the muscles of hand and forearm get tired faster, too, which, after all does not change much in effectiveness, even contrary—the longer one works the more cramped and crippled one gets in his position to balance the weight. This is improved by the invented machine which puts the coils in an angle, thus achieving a longer leverage effect with a longer hammer. On the invented machines that were set up yet the Hammer is by this effect around an inch longer than one of a conventional tattoo machine, which has the same measurements. This of course gives it a lot more power, since it's leverage is way bigger, still keeping the invented machine within the same sizes as a conventional machine.

BACKGROUND OF THE INVENTION

1. Field of the Invention

The invention relates to an improved way of applying pigments or dye or other fluids such as medical solutions or similar subcutaneously or intradermal into human or animal skin or into other matter like leather or plastics.

2. Discussion of the Prior Art

Tattoo machines and related devices are shown in some following representative patents listed below:

| US Patent Reference | | | |
|---|---|---|---|
| | 196747 | November 1877 | Edison |
| | 464801 | November 1891 | O'Rilly |
| | 4159659 | July 1979 | Nightingale |
| | 5054339 | October 1991 | Yacowitz |
| | 5551319 | September 1996 | Spaulding et al. |
| | 6282987 | March 2001 | Moniz |

May also be used as reference in the prior art: Machinegun Magazine published by eikon device inc. at www.machinegunmagazine.com or www.eikondevice.com Machine gun magazine #1, printed 2001 by eikon device, 692 Mc Kay st, Kingston, ON, Canada K7M 7G2, pages 6/7

Machine gun magazine #2, printed 2002 by eikon device, 692 Mc Kay st, Kingston, ON, Canada K7M 7G2, pages 28/29

Machine gun magazine #5, 2004 eikon device, 692 Mc Kay st, Kingston, ON, Canada K7M 7G2Z Machine gun magazine #6, 2005 eikon device, 692 Mc Kay st, Kingston, ON, Canada K7M 7G2, pages 7-9

The efficiency of tattooing devices relies on the manner in which the color solution or pigment is pushed into the skin by a needle or needle group. Therefore the device must overcome the opposition of the skin while penetrating it. The common way to do so is to use a needle or needlegroup which hits the skin in a linear way.

The loose end of the armature bar of an electromagnetic coil powered machine moves on a circular segment in the manner of a perpendicular tangent which issues above linear movement. This movement is naturally not straight since it is situated on a circle.

The armature bar of a D.C. Motor also runs in a linear course.

The power of the penetrating needle depends principally on the length of the armature bar (a.k.a. lever bar) and the distance between the armature bar and the front coil (a.k.a. air gap) that the armature bar has to overcome.

The efficiency of pushing colour into the skin depends further on the speed of the reciprocating needle. Only, the faster the machine runs the easier it is to cut and destroy the skin.

Other than that the functionality of a tattooing device depends on its size and weight.

The invention aims to improve the above mentioned components.

BRIEF SUMMARY OF THE INVENTION

The invented Tattoo machine puts the coils in an angle, which is compensated by an equivalent angle on the hammer. This is achieved by an angled block underneath the coils. The block can either be straight or in a stair-like shape, which would lead to a shorter, thus lighter back coil.

The inclined plane makes sure that the effective length of the hammer is bigger while the machine gets shorter in comparison.

It is an object of the invention to provide an improved electromagnetically driven electrical marking device or tattoo machine which follows the arc principle: the armature bar moves on a circular segment, only that the radius of the circle does not move on a horizontal plane but on a plane issued by a positive angle. The needlebar attached to the armature bar moves forward while it is pushed downwards. The needle itself is held by rubber bands in a fixed course. The color is literally lifted into the skin, contrary to being pushed in the skin in a linear way.

It is at the same time an object of the invention to provide an electromotor driven tattoo machine (rotary machine) which follows that same arc principal.

It is another object of the invention to provide the machine with a unique shaped, bent hammer in order to achieve that arc principle and to keep the height of the machine as small as possible.

It is another object of the invention to put the coil(s) of an electromagnetically driven tattoo machine at an angle in order to reduce the size and weight of the tattoo machine and therefore the leverage effect on the operator's hand.

It is another object of the invention to use different sized coils mounted on an angled, in a stair like manner composed assembly by using a lower back coil in the case of using two coils, in order to reduce size and weight.

It is another object of the invention to provide a hammer that is proportionally longer because of using that angled configuration so as to enhance the leverage effect of the hammer.

It is another object of the invention to provide a machine that by the above mentioned improvements works more effectively allowing for a reduced number of penetrations of the needles into the skin which makes it easier on the skin.

BRIEF DESCRIPTION OF THE SEVERAL VIEWS OF THE DRAWINGS

On the drawing sheet there are 4 figures shown, FIG. 1A to FIG. 1D, three of them (FIGS. 1A, 1B and 1D) showing the invented machine, one (FIG. 1 C) showing a conventional tattoo machine for comparison purposes.

FIG. 1 A shows the invention from a side view in a set up manner, while in FIG. 1B the main components are listed separately.

Figure 2A:
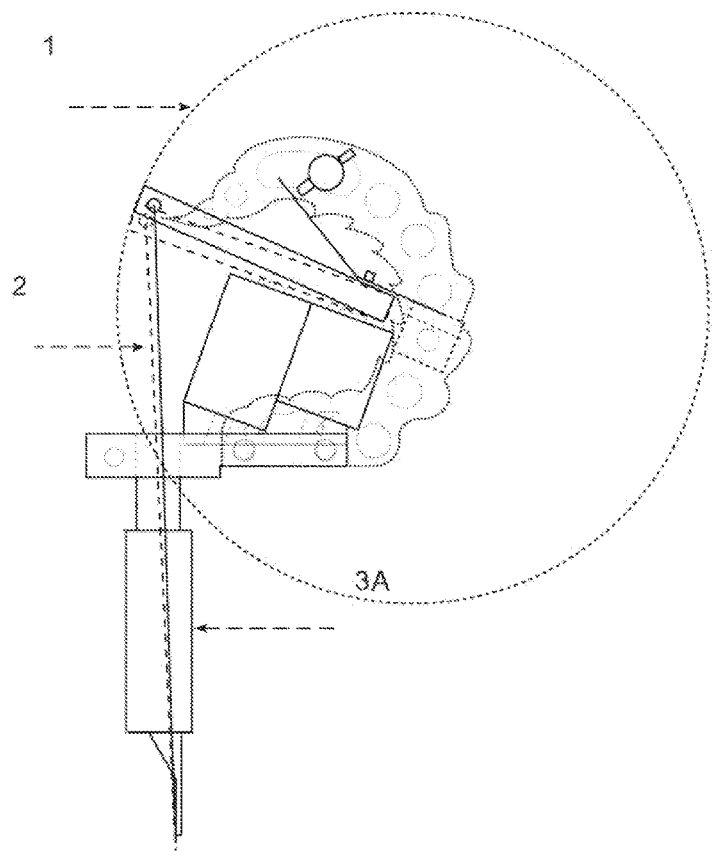

On the drawing sheet no. 1 4 figures are shown, FIG. 1A to FIG. 1D.

FIGS. 1 A, 1B and 1D show the invented machine.

FIG. 1 C shows a conventional tattoo machine for comparison purposes.

FIG. 1 A shows the invention from a side view in a set up manner.

FIG. 1B shows the main components in a structural side view.

FIG. 1 C shows a conventional machine from a front right side upper view.

FIG. 1 D shows the invented machine from a front right side upper view.

On the drawing sheet no. 2 3 figures are shown, FIG. 2A to FIG. 1C:

FIG. 2 A shows the machine from the side in order to illustrate the arc principle.

FIG. 2 B shows the machine from the side in order to illustrate the air gap.

FIG. 2 C shows the machine from the side in order to illustrate an angled base block without stair.

DETAILED DESCRIPTION OF THE INVENTION

FIG. 1 A shows the invention from a side view in a set up manner, while in FIG. 1B the main components are listed separately. The listing is the same like in FIGS. 1 C and 1 D to show the same parts in a 3-D view from the upper right front:

1 Top Binding Post with Contact screw
2 Front Spring
3 Hammer/Lever Bar
4 Rear Spring
5 Front Coil
6 Rear Coil
7 Spring Mount, in FIGS. 1B and 1 D attached to the Frame Side Plate
8 Yoke
9 Frame Base A tattoo machine is usually set up from three main frame parts, the Frame Base (see FIG. 1 B,C,D: 9), the Frame Side Plate and the Spring Mount (1B/7), which is in this case attached to the Side Plate in a specific angle. In this case that angle is 25 degrees.

On the Frame Base (1B/9) the Yoke (1B/8) is attached. This one is in a stair-like manner in an angle milled iron block, whose angle is around 3-4 degrees less than that of the spring mount. (The spring mount has some degrees more to ensure that there is enough spring tension, thus the backspring does not have to be bent which would result in spring tension loss after a while.)

On the Yoke the Front Coil (1B/5) and the Rear Coil (1B/6) are mounted. The Rear coil is smaller in height than the Front coil, which is compensated by the stair of the Yoke.

The Yoke makes sure that
a) the coils stay in their specific angle and
b) through the stair-like construction the rear coil can be made smaller than the front coil, making sure that they have the same upper level. Through this, the Rear Coil is lighter than a similar one on a conventional machine which helps on the leverage effect on the hand (for a better understanding you can see a set-up with tube in FIG. 2A, 3A refers on the tube).

This Part of the Invention, the smaller Rear Coil, is not new, other machines work with a stair like set-up already (though without an angle), usually custom made ones, since it seems to be to complicated for industrial production.

Figure 2B:
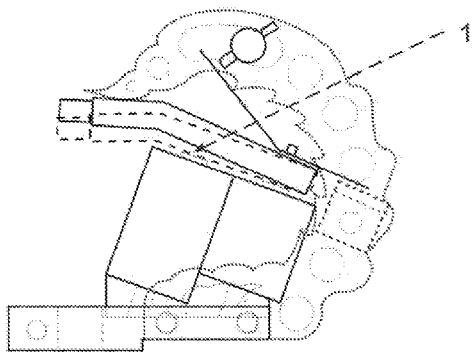
Figure 2C:
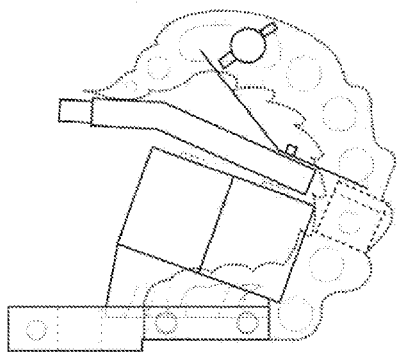

There can be also the case of one, or two coils of the same size, which are attached to a, in this case not in a stair-like construction, machined yoke or likewise construction (FIG. 2C).

The Improvement is the angle, making sure that the Hammer (1B/3), which is mounted on the Spring mount with the Front (1B/2) and the Rear Spring (1B/3), can be made longer in comparison to other tattoo machines.

To compensate the angle of the coils, the Hammer is bent in an equivalent angle, thus achieving that the end of the Hammer, the so called Armature Pin (not specifically shown in the drawing), which holds the needlebar, is in a more or less horizontal plane.

It has shown, that through the angle of the whole set-up and particularly of the Spring Mount, there is a slight forward motion—on a horizontal plane—of the armature pin (FIG. 2A/1).

This forward motion, coming from the effectively circular motion of the Hammer (FIG. 2A/1), might be on the short way to overcome the air gap (FIG. 2B/1) only around 1/40 to 1/30 of an inch (depending on the angle), but evidently it has a positive effect on the way that the needles penetrate the skin, which is also part of the invention.

The needles are not hitting the skin in the always same angle, but in a diving motion (FIG. 2A/2), which seems to be easier for the skin to deal with.

This again comes together with the hammer, which has through its angle a certain inertness, which gives its motion a whip-like effect, it pushes the ink into the skin with more impact.

The following numbers match FIG. 1B to D
1 Top Binding Post with Contact screw
2 Front Spring
3 Hammer/Lever Bar
4 Rear Spring
5 Front Coil
6 Rear Coil
7 Spring Mount, in FIGS. 1B and 1D attached to the Frame Side Plate
8 Yoke
9 Frame Base The tattoo machine according to the invention as seen in a set-up manner in FIG. 1A and separately explained in FIG. 1B consists of a Frame Base 9 at which the frame side plate and the spring mount 7 are attached, the dotted lines at the front end of 9 show the spring vise. The spring mount itself is attached at a 25 degree angle towards the side plate. On the frame base the stair-like milled yoke 8 is attached in a milled slot with a screw. The coils 5,6 are attached to the yoke with threaded pins, as shown in 8 with dotted lines. The smaller rear coil 6 equalizes the size of the higher front coil 5 through the stair in the yoke. The angle of the yoke stairs is around 3 degrees smaller than that one of the spring mount. A bent armature bar 3 is attached with a back spring 4 to the spring mount and is in loose contact via the front spring 2 with the adjustable contact screw 1.

FIG. 2A shows the circular motion (arc principle) 1 of the hammer, which is in this figure not explicitly bent for easier depiction.

FIG. 2 A 2 shows the uplift of the needle while it is pushed forward, explaining the diving motion.

FIG. 2 A 3A shows the needle holding tubular device.

FIG. 2B 1 shows the above mentioned air gap.

FIG. 2 C shows a machine without a stair in the yoke.

As shown in FIGS. 1C and D, the differences of a conventional tattoo machine and the invention are clearly described and the above described or depicted is to be considered as illustrative only in order to understand the principles of the invention.

An electric motor driven (rotary) machine is not explicitly depicted but follows the same principles as the invention and is therefore considered being deducible.

Any changes and derivations from the above displayed invention regarding sizes, measurements, angles, form and shape and processed matter are considered to be an interpretation and are regarded to be within the scope of the invention.

To those skilled in the art it is evident that components for the functioning of an electromagnetically driven tattoo machine are not assertively mentioned or described, since they are regarded general knowledge. This is not a deficiency within the explanation of the invention.

I claim:

1. A tattoo marking device, comprising:
   (a) a driver;
   (b) a frame that supports said driver, said driver powering the marking device;
   (c) an armature secured with respect to said frame, said driver causing said armature to oscillate;
   (d) a needle member having a needle member axis, said needle member coupled to said armature, such that oscillation of said armature results in reciprocation of said needle member in a path with components which are oblique and axial with respect to said needle axis; and
   (e) a needle guide mounted on said frame and through which said needle member reciprocates, wherein said driver comprises a front electromagnetic coil and a rear electromagnetic coil, a spring biases said armature away from said front electromagnetic coil and said rear electromagnetic coil, such that when said front electromagnetic coil and said rear electromagnetic coil are energized, said armature pivots toward said front electromagnetic coil and said rear electromagnetic coil, and wherein said frame comprises a frame base and the marking device further comprising a yoke that supports said front electromagnetic coil and said rear electromagnetic coil at an acute angle from said frame base.

2. The tattoo marking device of claim 1, wherein said front electromagnetic coil and said rear electromagnetic coil differ in size and said yoke is shaped to align said front electromagnetic coil and said rear electromagnetic coil.

3. The tattoo marking device of claim 2, wherein said yoke is generally stair-shaped.

4. The tattoo marking device of claim 1, wherein said needle member comprises a plurality of needles.

5. The tattoo marking device of 1, wherein said armature is oriented at an acute angle to a surface of said frame adapted to be positioned against skin during tattooing.

6. The tattoo marking device of claim 5, wherein said acute angle is generally in a range about 25 degrees.

* * * * *